Oct. 2, 1956 G. J. VON ABRAMS Plant Pat. 1,522
ROSE PLANT
Filed Oct. 31, 1955
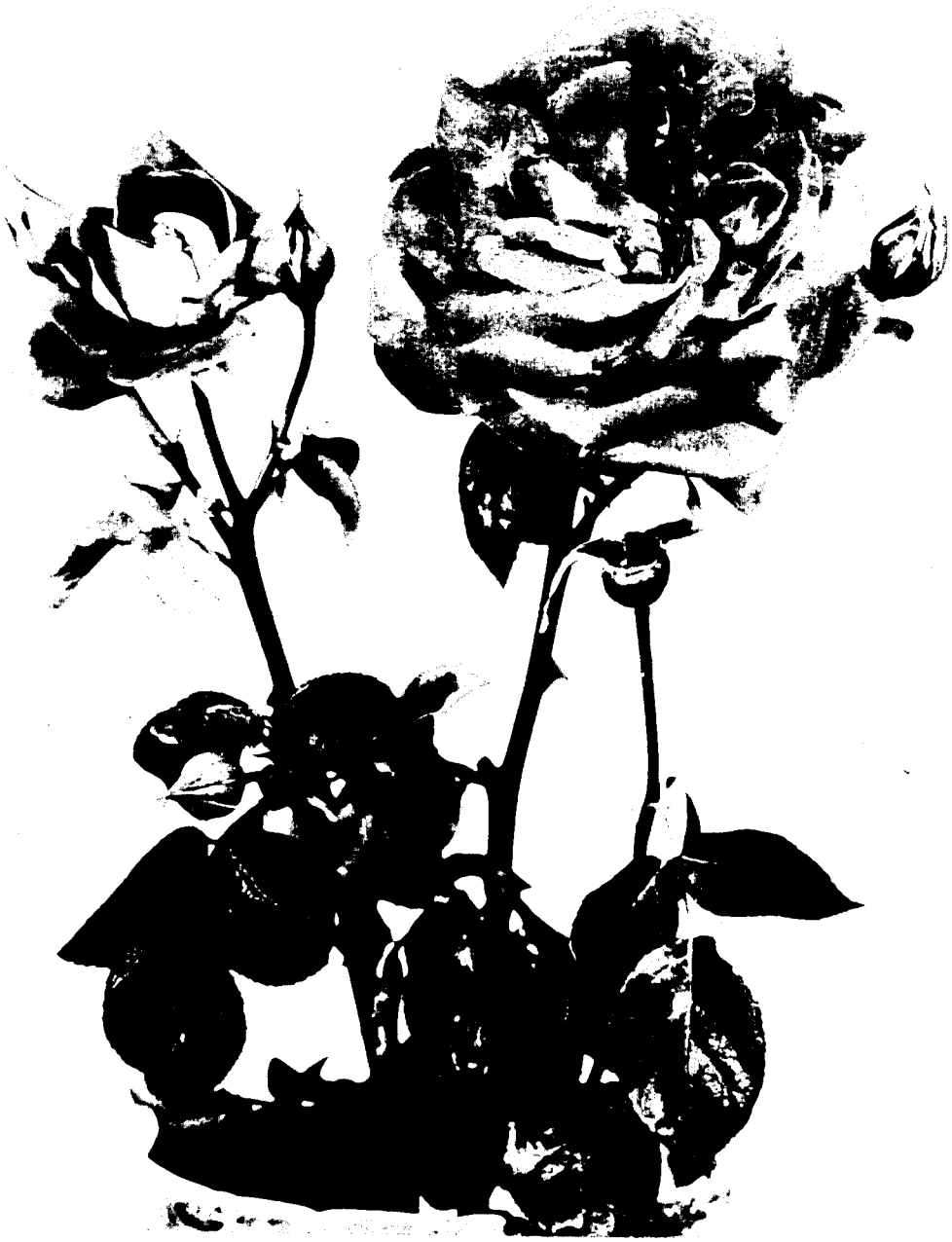
Inventor
G. J. Von Abrams
By J. Robb & Robb
Attorneys.

United States Patent Office

Plant Pat. 1,522
Patented Oct. 2, 1956

1,522

ROSE PLANT

Gordon J. Von Abrams, Scappoose, Oreg., assignor to Eldon Pinkeney Dering, doing business under the name of Peterson & Dering, Scappoose, Oreg.

Application October 31, 1955, Serial No. 544,100

1 Claim. (Cl. 47—61)

The present invention relates to a new and distinct variety of rose plant of the hybrid tea class, which was originated by me by crossing the variety "Applause" (Plant Patent No. 829) with the variety "Peace" (Plant Patent No. 591).

As the result of this breeding, I have produced a new and improved rose variety having the following general phenotypic characteristics:

(1) Vigorous habit of growth, medium tall (up to 4 feet) and somewhat open in habit;

(2) Heavy canes which frequently produce cyme-like inflorescence bearing as many as 15 blooms, each of which is borne on a long and strong stem;

(3) Globular bud which is small in proportion to the very large open flower;

(4) Free and continuous flowering habit throughout the growing season; and (5) A unique combination of form, size and color of the flowers which are distinct from any other rose in commerce of which I am aware.

In comparison with its seed parent "Applause," my new variety differs therefrom by the tendency of its plant to be somewhat more open in habit, with its foliage slightly less glossy and lighter in substance, and with larger flowers which are more regular in form and very different in color, being less red and more blue in general color effect, and being a reverse bi-color.

As compared with its pollen parent "Peace," the plant of the new variety is generally not as tall as "Peace," and its foliage is less glossy, less wrinkled, broader in outline and lighter in texture, with smaller stipules having points turned out at a greater angle. While the flower of my new variety is similar in form to that of this parent, it has more petals and the color is very different, containing less yellow, more red and blue, and is more distinctly a reverse bi-color.

Asexual reproduction of the new variety by bud-grafting, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Hardy; bush; outdoor; seedling; for cut flowers and for garden decoration.
Class: Hybrid tea.
Parentage: Seedling.

*Seed parent.*—"Applause."
*Pollen parent.*—"Peace."
Propagation: Holds its distinguishing characteristics through succeeding propagations by bud-grafting.

FLOWER

Locality where grown and observed: Scappoose, Oregon.
Flowers borne: Sometimes singly, but generally 3 or more to stem, and frequently in irregular cymes ranging to 15.
Quantity of bloom: Free, outdoors.
Continuity: Continuous during the growing season.
Fragrance: Slight.
Bud:

*Peduncle.*—Medium length; from 5 to 8 cm. in length; medium heavy; from erect to stiff; medium roughness; with numerous Red glandular cilia. Color—Reddish Green.

*Before calyx breaks.*—Size—medium length; from 2 to 3 cm. in length. Form—short pointed, with conspicuous neck; outer surface has numerous glandular cilia; lateral margins of alternate sepals generally bear very slender foliaceous appendages; most sepals bear terminal foliaceous appendages, generally less than ¼ of bud length, but sometimes reaching 2 cm. in length, in which latter case they are deeply serrate. Color—near Chromium Green, Plate XXXII, 31".i (Ridgway), flushed with Maroon.

*As calyx breaks.*—Color—near Old Rose, Plate XIII, 1'.b (Ridgway), flushed and lined with Pomegranate Purple, Plate XII, 71.i (Ridgway).

*As first petal opens.*—Size—large. Form—short pointed, becoming globular. Color: outside—variable from Cardinal Red, Plate 822/2, page 168 (Wilson) to Tyrian Rose, Plate 24/2, page 24 (Wilson); generally near Rose Madder, Plate 23/1, page 23 (Wilson), heavily flushed toward apex with Rose Red, Plate 724, page 158 (Wilson), with veins of Rose Red, Plate 724, page 158 (Wilson) or darker, and with base of Lemon Yellow, Plate 4/2, page 4 (Wilson), suffused upward; inside—from near Rose Red, Plate 724, page 158 (Wilson) to Rose Red, Plate 724/2, page 158 (Wilson), with darker veins and with basal spot of near Lemon Yellow, Plate 4/1, page 4 (Wilson), usually suffused upward.

*Opening.*—Opens up well except under extreme cold, wet conditions.

Bloom:

*Size (when fully open).*—From large to very large; from 10 to 18 cm.

*Petalage.*—Double; from 50 to 60 petals; arranged regularly.

*Form.*—High-centered to maturity; petals at first being cupped tightly inward, gradually rolling outward at tip and then sharply along apical edges; rolled lightly outward around entire margin at maturity.

Petals:

*Texture.*—Moderately thick; soft; with inside and outside satiny.

*Shape.*—Outside—obovate; margin generally entire. Intermediate—obovate, with base somewhat wedge-shape; margin entire. Inside—obovate, with base near spatulate; apical margin entire or irregular.

This description of a newly opened flower was made from a rose grown outdoors in the month of August, at Scappoose, Oregon:

*Color.*—Outer petal: outside surface—from Crimson, Plate 22/2, page 22 (Wilson) to Crimson, Plate 22/3, page 22 (Wilson), flushed at base with Barium Yellow, Plate 503, page 131 (Wilson); inside surface—between Tyrian Purple, Plate 727, page 159 (Wilson) and Rose Red, Plate 724, page 158 (Wilson), flushed at base with Aureolin, Plate 3, page 3 (Wilson). Intermediate petal: outside surface—Carmine, Plate 21/2, page 21 (Wilson), flushed at base with from Mimosa Yellow, Plate 602, page 143 (Wilson) to Mimosa Yellow, Plate 602/2, page 143 (Wilson); inside surface—near Tyrian Purple, Plate 727, page 159 (Wilson), flushed at base with Aureolin, Plate 3, page 3 (Wilson). Inner petal: outside surface—Carmine, Plate 21/3, page 21 (Wilson), washed irregularly with Rose Madder, Plate 23/2, page 23 (Wilson), and flushed at base with from Mimosa Yellow, Plate 602, page 143 (Wilson) to Mimosa Yellow, Plate 602/2, page 143 (Wilson); inside surface—from Rose Red, Plate 724, page 158 (Wilson) to Rose Red, Plate 724/1, page 158 (Wilson), flushed at base with Aureolin, Plate 3, page 3 (Wilson). General color effect: from Rose Red, Plate 724, page 158 (Wilson) to Rose Red, Plate 724/1, page 158 (Wilson), with distinctly lighter reverse.

This description was made from a rose that was open for 3 days outdoors in the month of August, at Scappoose, Oregon:

*Color.* — Outer petal: outside surface — from Magenta, Plate 27/2, page 27 (Wilson) to Magenta, Plate 27/3, page 27 (Wilson), flushed at base with Baryta Yellow, Plate IV, 21.f (Ridgway); inside surface—Magenta, Plate 27, page 27 (Wilson), flushed at base with from Aureolin, Plate 3, page 3 (Wilson) to Aureolin, Plate 3/3, page 3 (Wilson). Intermediate petal: outside surface—Rose Bengal, Plate 25/3, page 25 (Wilson), flushed upward from base with Naples Yellow, Plate 403/3, page 121 (Wilson), and with basal spot of Aureolin, Plate 3, page 3 (Wilson); inside surface—Solferino Purple, Plate 26, page 26 (Wilson), flushed at base with from Aureolin, Plate 3, page 3 (Wilson) upward to Aureolin, Plate 3/3, page 3 (Wilson). Inner petal: outside surface—Rose Bengal, Plate 25/2, page 25 (Wilson), flushed upward from base with Aureolin, Plate 3/3, page 3 (Wilson); inside surface—Solferino Purple, Plate 26, page 26 (Wilson), flushed at base with from Aureolin, Plate 3, page 3 (Wilson) upward to Aureolin, Plate 3/3, page 3 (Wilson). General color effect—Solferino Purple, Plate 26, page 26 (Wilson), with silver-flushed reverse; the description of the intermediate petal applies to the majority of the petals of the bloom, and therefore most closely represents the general color effect, and indicating the degree of contrast between the two surfaces of the petals.

*Behavior.*—Petals drop off cleanly; color becomes gradually lighter during senescence; size and color maintained well in hot, dry weather,

*Flower longevity.*—On bush in garden—6 days in August. Cut roses grown outdoors and kept at livingroom temperatures—5 days in August.

REPRODUCTIVE ORGANS

Stamens: Moderately numerous; arranged regularly around margin of receptacle; free of pistilate parts.

Filaments: Medium length (about 1cm.); nearly all with anthers. Color (mature anthers)—from near Indian Yellow, Plate 6, page 6 (Wilson) to Indian Yellow, Plate 6/3, page 6 (Wilson).

Pollen: Normally abundant. Color—gold.

Pistils: Many.

Stigma: Color—pink.

Styles: Quite even; medium length (from 0.7 to 1 cm.); medium diameter; loosely bunched.

Ovaries: Enclosed in receptacle.

Fruit: Globular; smooth surface; walls medium thick and fleshy. Color (at maturity)—Orange.

Seeds: Moderate number; medium size.

Sepals: Persistent; long (about 1.5 x 4 cm.); spear-shape; recurved. Color: outer surface—near Parrot Green, Plate VI, 31.k (Ridgway); inner surface — Light Fluorite Green, Plate XXXII, 33".d (Ridgway), with Maroon flush.

PLANT

Foliage:

*Leaves.*—Compound of 3 to 7 leaflets, but usually 5; abundant.

*Leaflets.*—Size—large (to about 9 x 7 cm.). Shape—oval, with apex mucronate. Base—slightly cordate. Margin—simply serrate. Substance—from moderately heavy to heavy. Texture—semi-glossy.

*Color.*—Mature: upper surface—near Yew Green, Plate XXXI, 27".m (Ridgway); under surface—near Light Cress Green, Plate XXXI, 29".i (Ridgway). Young: upper surface—near Hay's Maroon, Plate XIII, 1'.m (Ridgway), flushed with Green; under surface—near Mineral Red, Plate XXVII, 1".k (Ridgway).

*Rachis (the supporting stem of the compound leaf).*—Heavy. Upper side—grooved and bearing several grandular cilia; under side—sparsely thorned and ciliated.

*Stipules.*—Medium size (about 2 x 1 cm.); with points of medium length (about 5 mm.), turning out at about 45°.

*Disease Resistance.*—Slightly better than average resistance to mildew and blackspot, and similar to pollen parent "Peace," in this respect, as compared with other varieties grown under comparable cultural conditions at Scappoose, Oregon.

Growth:

*Habit.*—Upright bush; somewhat open; moderately branched.

*Growth.*—Free.

*Canes.*—Heavy.

*Main Stems.*—Color—Gray-Green. Thorns—several; hooked downward; medium length, with long oval base. Color — gray. Prickles — none. Hairs—none.

*Branches.*—Color—Dull Bronzy Green. Thorns—several; hooked downward; medium length. Color—reddish. Prickles—none. Hairs—none.

*New Shoots.* — Color — Bright Bronzy Red. Thorns—moderately numerous; nearly straight; medium length. Color—Red. Prickles—none. Cilia—few.

I claim:

A new and distinct variety of rose plant of the hybrid tea class, substantially as herein shown and described, characterized particularly as to novelty by its vigorous, medium tall and somewhat open habit of growth, its heavy canes which frequently produce cyme-like inflorescence bearing many blooms, each on a long, strong stem, its relatively small globular buds which open to very large flowers, its free and continuous flowering habit throughout the growing season, and the unique combination of form, size and distinctive color of its flowers.

No references cited.